United States Patent [19]

Quadro

[11] Patent Number: 4,839,366

[45] Date of Patent: Jun. 13, 1989

[54] METHYLTHIOQUINOLYL GUANIDINE DERIVATIVE, PROCESS OF PREPARATION THEREOF AND PHARMACEUTICAL COMPOSITIONS THEREFROM

[75] Inventor: Giuseppe Quadro, Milan, Italy

[73] Assignee: Chiesi Farmaceutici S.p.A., Parma, Italy

[21] Appl. No.: 159,226

[22] Filed: Feb. 23, 1988

Related U.S. Application Data

[63] Continuation of Ser. No. 828,314, Feb. 11, 1986, abandoned, which is a continuation-in-part of Ser. No. 593,037, Mar. 23, 1984, abandoned.

[30] Foreign Application Priority Data

Apr. 6, 1983 [IT] Italy ............................ 20468 A/83

[51] Int. Cl.$^4$ .................... A61K 31/47; C07D 401/12
[52] U.S. Cl. ................... 514/312; 546/157; 546/168; 546/169; 546/170
[58] Field of Search ............... 514/312, 313; 546/157, 546/159, 162

[56] References Cited

U.S. PATENT DOCUMENTS 4,293,549 10/1981 Rachlin et al. ..................... 514/313
4,680,300 7/1987 Nelson et al. ..................... 546/157

OTHER PUBLICATIONS

Burger, "Medicinal Chemistry", Interscience Publishers, N.Y. (2nd Ed.), p. 75 (1960).
Labrecque et al., *Pharmacology*, pp. 169–174 (1982).

Primary Examiner—Anton H. Sutto
Assistant Examiner—E. Bernhardt
Attorney, Agent, or Firm—Bucknam and Archer

[57] ABSTRACT

The compound of formula (I):

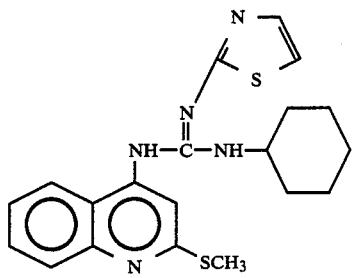

N-cyclohexyl-N''-4-(2-methylthioquinolyl)-N'-2-thiazolyl-guanidine and pharmaceutically acceptable salts thereof is a valuable antiinflammatory, analgesic and antipyretic agent.

The compound of the invention may be formulated with conventional pharmaceutically acceptable carriers or diluents to provide a pharmaceutical composition.

4 Claims, No Drawings

METHYLTHIOQUINOLYL GUANIDINE DERIVATIVE, PROCESS OF PREPARATION THEREOF AND PHARMACEUTICAL COMPOSITIONS THEREFROM

This application is a continuation of U.S. Ser. No. 828,314 filed Feb. 11, 1986, now abandoned, which was a continuation-in-part of U.S. Ser. No. 593,037 filed Mar. 23, 1984, now abandoned.

The present invention relates to a new compound of formula (I):

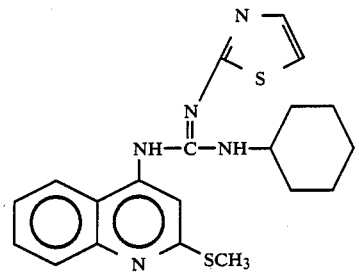

N-cyclohexyl-N''-4-(2-methylthioquinolyl)-N'-2-thiazolyl-guanidine.

The present invention relates also to pharmaceutically acceptable salts of compound I with organic acids such as acetic, succinic, tartaric, citric acid or inorganic acids such as hydrochloric, hydrobromic, sulfuric acid.

The compound of formula I has excellent antiinflammatory, analgesic and antipyretic activities and is a potent inhibitor of the activity of prostaglandin-synthetases.

In the U.S. Pat. No. 4,293,549 are described analogous N-4-quinolyl-guanidine derivatives; the best one of the series appears to be N-cyclohexyl-N''-4-(2-methylquinolyl)-N'-2-thiazolyl guanidine (SR 1368), subsequently also referred as timegadine.

It has now been surprisingly found that the compound of formula I of the present specification shows advantageous therapeutic characteristics with respect to compounds described in the above cited U.S. patent and particularly with respect to SR 1368 (timegadine).

The compound of the invention may be prepared by a process which comprises the following steps:
1—reacting a 2-methylthio-4-aminoquinoline (II) with cyclohexylisocyanate (III);
2—subsequent dehydration of the resulting urea to carbodiimide, using triphenylphosphine and triethylamine in carbon tetrachloride;
3—reacting the resulting compound with 2-aminothiazole.

The reaction scheme is reported hereinbelow.

SCHEME I

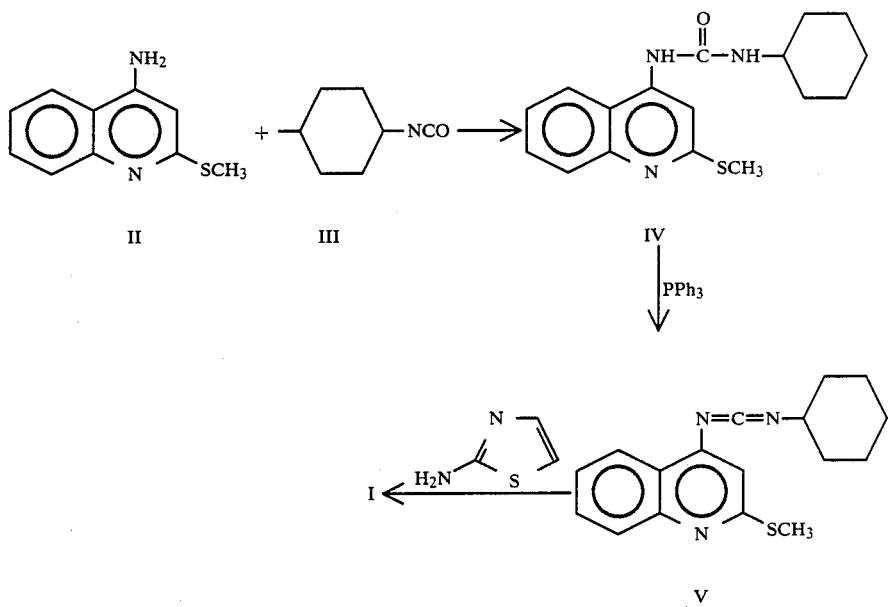

The starting 2-methylthio-4-aminoquinoline may be suitably prepared according to the following scheme:

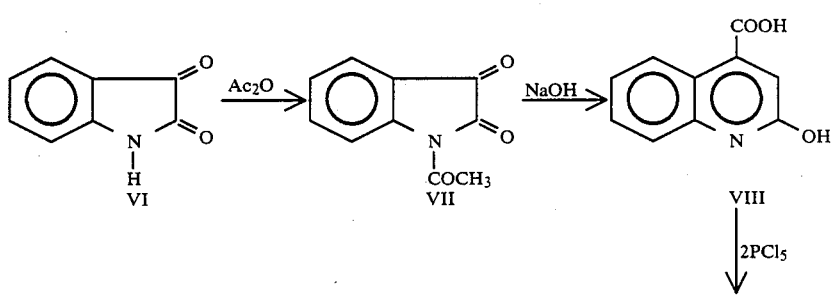

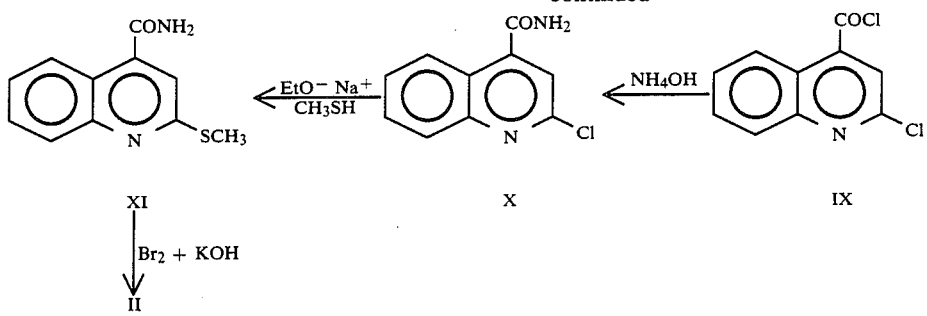

The 2-hydroxy-4-quinolinecarboxylic acid (VIII), obtained by rearrangement of N-acetyl-isatin (VII), is converted into the 2-chloro-4-quinolinecarboxylic acid amide by treatment of $PCl_5$ and $NH_4OH$.

The nucleophilic substitution of the chlorine atom at 2-position and the Hoffmann reaction give the starting compound (II).

The preparation of the compound of the invention is further illustrated by the following non-limiting examples.

PREPARATION 1

(a)

N-acetyl-isatin (VII)

50 g (0.34 moles) of isatin in 120 ml of acetic anhydride was heated to reflux for 30 minutes, with stirring.

The reaction mixture was kept overnight at room temperature: acetyl isatin precipitated in form of a yellow residue, which was recovered and washed with acetic anhydride.

After evaporation of the acetic anhydride, 20 g of a solid residue was obtained, which was acetylisatin (as it appeared by T.L.C.).

The two residues were combined, suspended in 200 ml of toluene and kept under stirring for 10 minutes, filtered and dried at 70° C.

The resulting orange solid was free from acetic anhydride.

M.p. 130°-133° [Lit. 140° C.].

Yield 84% (54 g).

T.L.C. ($PhCH_3$/AcOEt=75/25): slightly impure for isatin.

(b)

2-Hydroxy-4-quinolinecarboxylic acid (VIII)

25.2 g (0.286×2.2 moles) of NaOH tablets was dissolved in 500 cc. of water. The solution was heated to reflux, then 54 g (0.286 moles) of compound (VII) was added, in 4 portions.

The reaction mixture was refluxed for 1 hour. After cooling and acidification with concentrated HCl, a yellow-orange precipitate was obtained, which was recovered by filtration. Since it resulted slightly impure for the presence of isatin (checking by T.L.C.), the precipitate was poured in acetone, stirred for about 10 minutes (isatin is soluble in acetone while VIII is not) and filtered obtaining a yellow solid.

m.p. 250° C. [Lit. >340° C.].

yield 30.9 g (57%).

T.L.C. ($PhCH_3$/AcOEt: 75/25): single spot—Rf=0.

(c)

2-Chloro-4-quinolinecarboxylic acid chloride (IX)

23 g (0.122 moles) of compound (VIII) and 55.7 g (0.122×2 moles+10% excess) of $PCl_5$ were heated in oil-bath to 140°-150° C. for 1 hour, under stirring.

The produced $POCl_3$ was evaporated off, and a brownish residue was obtained which was crystallized from n-hexane, giving an almost colourless residue.

M.p. 85°-87° C. [Lit. 89°].

Yield: 27.8 g (quantitative on the crude product).

T.L.C. ($PhCH_3$/AcOEt: 75/25): single spot.

(d)

2-Chloro-4-quinolinecarboxylic acid amide (X)

200 cc. of a 32% $NH_4OH$ aqueous solution was cooled to 5° C.; then 27.8 g (0.123 moles) of compound (IX) dissolved in 100 cc. of toluene was added dropwise, with stirring, keeping the temperature between 5° and 10° C.

After completion of the addition, the reaction mixture was stirred for 10 minutes, then the precipitated amide was filtered off, giving a solid residue which was washed with water, filtered and finally crystallized from EtOH to give compound (I) in the form of a nearly colourless crystalline solid residue.

M.p.: 250°-252° C. [Lt. 238°-239° C.].

Yield: 23.4 g (92%).

T.L.C. ($\phi CH_3$/AcOEt=24/75/1): single spot.

(e)

2-methylthio-4-quinolincarboxylic acid amide (XI)

Sodium ethylate was prepared by dissolving 2.53 g (0.11 moles) of metallic Na in 120 ml of anhydrous ethanol.

The solution was cooled in ice-bath, then 7.92 g (0.165 moles) of $CH_3SH$ was insufflated.

22.5 g (0.11 moles) of (X) was added thereto under stirring and the mixture was heated to reflux for 3 hours.

After cooling the reaction mixture was poured in water.

The insoluble white-grey solid was filtered, washed with water and dried at 70° C.

The product was then crystallized from ethanol obtaining a colourless solid (XI)

M.P. 228°-229° C. (Lit 228.5°-229.5° C.).

Yield: 22.2 g (93%).

T.L.C. (EtOH/AcOEt/TEA=24/75/1): single spot.

2-methylthio-4-aminoquinoline (II)

34.2 g (0.612 moles) of KOH was dissolved in 150 cc. of water. The solution was cooled to 0° C., then 5.83 cc. (0.102 moles + 10% excess) of Br$_2$ was added, dropwise.

After about 10 minutes a suspension of 22.2 g (0.102 moles) of (XI) in 200 ml of water was added to the solution.

After the addition was completed the reaction mixture was stirred for 4 hours at room temperature then heated to a 80° C. in oil-bath for 1 hours.

The mixture was cooled in ice and the precipitated solid compound filtered and chromatographed on 300 g of SiO$_2$ (eluent PhCH$_3$/AcOEt=75/25) to give a colourless solid compound (II).

M.p. 103°–105° C. (Lit 99°–100° C.).

Yield: 6.5 g (34%).

T.L.C. (PCH$_3$/AcOEt=50/50): single spot.

NMR (CDCl$_3$): in agreement.

EXAMPLE 1

N-Cyclohexyl-N''-4-(2-methylthioquinolyl)-N'-2-thiazolylguanidine (I)

(1)

N-Cyclohexyl-N''-4-(2-methylthioquinoline)urea (IV)

1.81 g (0.034 moles + 10% excess) of 50% NaH was suspended in 100 cc. anhydrous toluene and 20 cc. anhydrous DMSO. 6.5 g (0.034 moles) of 4-amino-2-methylthioquinoline was added, then 5.64 cc (0.034 moles + 30% excess) of cyclohexylisocyanate was added dropwise.

The reaction mixture was heated to 80°–90° C. in oil-bath for 8 hours; the solvent was evaporated off, the residue was treated with water and the pH was adjusted to 5 with concentrated CH$_3$COOH. The resulting pale yellow residue (IV) was filtered and dried at 70° C.

M.p.: 207°–209° C.

Yield: 10.6 g (98%).

T.L.C. (PhCH$_3$/AcOEt=50/50): single spot.

N.M.R. (DMSO): in agreement.

The resulting urea was crystallized in the anhydrous form (Karl-Fisher Test: negative).

(b)

N'Cyclohexyl-N''-4-(2-methylthioquinolyline)carbodiimide (V)

10.6 g (0.034 moles) of IV and 10.05 g (0.038 moles) of Ph$_3$P were suspended in 100 cc. anhydrous CH$_2$Cl$_2$, and 3.4 cc (0.035 moles) of CCl$_4$ and 5 cc. (0.036 moles) of triethylamine were added.

The reaction mixture was refluxed for 5 hours, after which the solvent was evaporated off and the residue was extracted with hot toluene. The insoluble triethylamine hydrochloride was filtered on celite and the solvent was evaporated off, to give a thick brown oil (V).

Yield: (quantitative of the crude product) 12 g.

T.L.C. (PhCH$_3$/AcOEt=50/50): impure for triphenylphosphine.

N-Cyclohexyl-N''-4-(2-methylthioquinolyl)-N'-2-thiazolylguanidine, HCl (I)

To a solution of 12 g (0.034 theoric moles) of crude V in 100 cc. of anhydrous toluene, 3.4 g (0.034 moles) of 2-aminothiazole was added.

The reaction mixture was refluxed for 7 hours, after which the solvent was evaporated off and the residue was chromatographed on 300 g of SiO$_2$ (eluent PhCH$_2$/AcOEt=9/1), to give compound I as the free base, in the form of an orange oil (5.3 g).

The compound was dissolved in anhydrous EtOH and subjected to bubbling with gaseous HCl, to give the corresponding hydrochloride.

The ethanol was distilled off and the residue was treated with hot ethyl acetate and filtered, to give a solid yellow product.

M.p.: 221°–224° C.

Yield: 4.5 g of hydrochloride (31% on theoretical moles).

Chloride contents=99.78%.

T.L.C. ($\phi$CH$_3$/n-hexane/AcOEt=10/45/45): single spot; stationary phase=silica gel; detected by iodine vapour or exposition to UV light 254 nm.

N.M.R. (CDCl$_3$): in agreement.

Similar preparation of the compound of the invention was previously reported in our U.S. patent application Ser. No. 593,037.

The compound described in that disclosure, however, contained some impurities.

The present invention provides N-cyclohexyl-N''-(2-methylthioquinolyl)-N'-2-thiazolyl-guanidine as monohydrochloride with a melting point ranging from 221° to 224° C.

The compound object of the present invention has been characterized from the toxico-pharmacological point of view.

As reference compound was used timegadine, structurally related molecule previously described in the above cited U.S. Pat. No. 4,293,549 of Leo Pharmaceutical.

Acute toxicity

The toxicity for single administration has been determined by the oral route in IVa:NMRI (SPF) fasted male mice, with water ad libitum, 18 hours before the experiment. The approximate LD$_{50}$ values, determined by interpolation on Probits paper, are reported in Table 1.

TABLE 1

| Compound | LD$_{50}$ approx mg/kg |
|---|---|
| I | >1000 |
| Timegadine | >1000 |

Carrageenin paw edema in the rat

Paw edema was induced in male rats fasted for 18 h but with free access to water, by the method of WINTER et al. (Winter C. A. et al. Proc. Soc. Exp. Biol. Med. 111, 544, 1962) injecting 0.1 ml carrageenin 1% in physiological saline into the right hind paw aponeurosis.

60 min before induction of edema the drugs suspended in 0.2% Tween 80 aqueous solution were dosed by gastric tube (20 ml/Kg); the controls received the vehicle only.

The volume of the right paw was measured by plethysmography immediately before (time 0) and 1, 2, 3, 4, 6 h after subplantar injection of the irritant.

The area under the curve expressing the paw volume plotted against time (AUC) was calculated for each animal.

The results, expressed as percent inhibition of edema development in treated animals as compared to the controls and as ED$_{40}$ values obtained from the regression lines for dose-AUC, are reported in Table 2.

delivered by esophageal tube (suspension in 0.2% Tween 80 aqueous solution, 10 ml/Kg).

TABLE 2

| Treatment | Dose μmol/kg | % inhibition vs controls | | | | | | ED$_{40}$ μmol/Kg | Potency ratio relative to timegadine |
| --- | --- | --- | --- | --- | --- | --- | --- | --- | --- |
| | | 1 h | 2 h | 3 h | 4 h | 6 h | AUC | | |
| Compound I | 274 | 17 | 53** | 58** | 56** | 33** | 49.0** | 111 | 1.32 |
| | 91 | 13 | 51** | 48** | 42** | 17** | 37.3** | | |
| | 30 | 4 | 47** | 40** | 28** | 8 | 27.9** | | |
| timegadine | 274 | 33* | 55** | 58** | 57** | 44** | 52.9** | 147 | 1 |
| | 91 | 38* | 51** | 30** | 27** | 9 | 28.4** | | |
| | 30 | 17 | 18 | 11 | 15 | 4 | 12.3 | | |

Carrageenin-induced paw edema in the rat: effects of oral test compounds at different times after carrageenin application, on edema and on the areas under time-edema development curve (AUC). Statistical difference (Student's t): *P < 0.05; **P < 0.01

Phenylquinone writhings in the mouse

The method used was that of SIEGMUND et al. (Siegmund et al. J. Pharmacol. Exp. Ther. 119, 184, 1957) modified (Arzneim. Forsch. 31(1), 87, 1981).

Male mice, 19–22 g, fasted for 18 h with free access to water, received the test drugs suspended in 0.2% Tween 80 aqueous solution (10 ml/Kg) by esophageal tube, the controls receiving the vehicle only.

One hour later all the animals were given an intraperitoneal injection of 0.02% phenylquinone solution in 5% aqueous ethanol (10 ml/Kg).

A 'blind' observer recorded the number of writhings in each animal from the 5th to the 15th min after phenylquinone administration. The ED$_{50}$ values obtained from the dose-response curves are reported in Table 3.

Control animals received the vehicle only (10 ml/Kg).

Five hours after drug administration the rats were killed.

The stomach was slit along the lesser curvature, washed under running water and examined for haemorrhagic lesions in the glandular part of the mucosa: these lesions will be conventionally defined as 'ulcers'.

The following were recorded:

(a) the sum of the maximum diameters of all the ulcerated spots;
(b) the number of ulcerated spots.

The UD$_{50}$ was calculated by the method of LITCHFIELD and WILCOXON (Litchfield J. T., Wilcoxon F. J. Pharm. Exp. Ther. 96, 99–113, 1949), all animals with gastric lesion whose sum (a) was 2 mm or more

TABLE 3

| Treatment | Dose μmol/Kg | No. of anim. | No. of writhings (X ± SE) | % inhibition vs controls | ED$_{50}$ μmol/Kg | Potency ratio relative to timegadine |
| --- | --- | --- | --- | --- | --- | --- |
| Vehicle | — | 12 | 36.8 ± 2.3 | — | — | — |
| Compound I | 164 | 10 | 1.3 ± 0.5 | 96.5** | 18.7 | 3.1 |
| | 55 | 10 | 7.6 ± 2.4 | 79.3** | — | — |
| | 18.3 | 10 | 19.5 ± 4.8 | 47.0** | — | — |
| timegadine | 164 | 10 | 6.6 ± 2.9 | 82.1** | 58.9 | 1 |
| | 55 | 10 | 23.4 ± 4.6 | 36.4* | — | — |
| | 18.3 | 10 | 27.2 ± 4.1 | 26.1* | — | — |

Analgesic activity on phenylquinone-induced writhings in the mouse, by oral administration. Statistical difference from controls (Student's t): *P < 0.05; **P < 0.01

Acute effect on gastrointestinal tract: gastric ulcers in the rat

Male rats weithing 250–280 g were starved for 18 h but allowed free access to water and the drugs were being rated as 'ulcerated'.

The results are reported in Table 4.

TABLE 4

Gastric ulcerogenic effects on the rat after single oral administration of compound I or Timegadine.
Rats with gastric ulcers: ulceration 2 mm and over (sum of maximum diameters).

| Treatment | Dose μmol/Kg | No. of anim. | Gastric ulcers (X ± SE) | | Rats with gastric ulcers | UD$_{50}$ μmol/Kg | Potency ratio relative to timegadine |
| --- | --- | --- | --- | --- | --- | --- | --- |
| | | | No. | mm | | | |
| Compound I | 922 | 10 | 4.8 ± 1.5 | 8.7 ± 3.5 | 5/10 | 887 | 0.47 |
| | 461 | 10 | 2.1 ± 1.0 | 3.8 ± 1.8 | 4/10 | | |
| | 230 | 10 | 0.6 ± 0.3 | 1.2 ± 0.8 | 1/10 | | |
| | 115 | 10 | 0.5 ± 0.3 | 0.5 ± 0.3 | 1/10 | | |
| Timegadine | 922 | 10 | 9.4 ± 1.8 | 18.5 ± 4.4 | 9/10 | 413 | 1 |
| | 461 | 10 | 4.4 ± 1.5 | 6.7 ± 2.3 | 6/10 | | |
| | 230 | 10 | 0.8 ± 0.3 | 1.3 ± 0.7 | 2/10 | | |
| | 115 | 10 | 0.3 ± 0.2 | 0.4 ± 0.2 | 0/10 | | |

Gastric ulcerogenic effects on the rat after single oral administration of compound I or Timegadin.
Rats with gastric ulcers: ulceration 2 mm and over (sum of maximum diameters).

From the UD$_{50}$/ED$_{40}$ ratio (antiinflammatory activity values obtained from the regression lines for dose—AUC) the therapeutic index were calculated (Table 5).

TABLE 5

Determination of the therapeutical index (T.I.)

| Treatment | $UD_{50}$ μmol/Kg | $ED_{40}$ μmol/Kg | T.I. ($UD_{50}/ED_{40}$) | T.I. relative to timegadine |
|---|---|---|---|---|
| Compound I | 887 | 111 | 7.99 | 2.82 |
| timegadine | 413 | 147 | 2.83 | 1 |

In animal experiments the compound of the present specification has shown interesting therapeutical effects.

Compound I proved to have antiinflammatory and analgesic activities higher than those of timegadine (the most active of a series of structurally related compounds) together with a lesser gastric irritant potential.

This feature is particularly interesting because gastrointestinal side effects and gastric injury are the commonest and most important indesirable concomitants of antiinflammatory therapy with non-steroidal anti-inflammatory agents.

The therapeutic index, i.e., the ratio of antiinflammatory potency to gastrointestinal damage of Compound I is 2.82 higher than that of timegadine.

The present invention refers also to all the industrially applicable aspects connected with the use of the compound of formula I in therapy as antiinflammatory, analgesic and antipyretic agent.

The present invention refers also to pharmaceutical compositions containing as active principle a compound of formula (I), as above defined, as such or in form of a pharmaceutically acceptable salt, in admixture with at least one pharmaceutically acceptable excipient.

The composition can be administered by oral, rectal, parenteral or topic route, respectively in form of capsules, tablets or similar formulations, suppositories, vials, cream or gels.

For the preparation of pharmaceutical formulations for the oral administrations in unit dose, the active principle can be mixed with a solid powdered excipient such as lactose, saccharose, sorbitol, mannitol; potatoes, cereals or maize starch or amylopectin, a cellulose or gelatine derivative, and it can moreover contain lubricants such as talc, magnesium or calcium stearate, polyethylenglycol or silica.

The tablets can be differently coated according to well known method in the pharmaceutical practice. Hard gelatine capsules can contain granulates of the active principle together with solid, powdered excipients such as lactose, saccharose, sorbitol, mannitol, starches (of the above mentioned kind), cellulose or gelatine derivative, and they can also contain stearic acid or magnesium stearate or talc.

Unit doses for rectal administration can be in form of suppositories containing the active principle in combination with a neutral fatty carrier (for instance glycerides of fatty acids) or with hydrosoluble or self-emulsifiable (for instance, polyethylenglycols mixture).

For injectable formulations for parenteral administration the excipients can be a pharmaceutically acceptable sterile liquid such as water or an aqueous solution of polyvinylpyrrolidone or even an oil such as peanut oil and optionally a stabilizing and/or buffer agent.

The active principle can be dissolved into the liquid and filter sterilized before of the distribution into vials or it can be suitably sterilized, being therefore added vials of liquid for injections in the packagings to restore the solution before use.

A local anaesthetic, when necessary, can be added to the excipients both in the case of suppositories and of vials formulations.

The unit dose for the above described formulations will range from 150 to 300 mg of active principle (even up to 500 mg for suppositories).

For the preparation of formulations for topical use, for creams or unguents fatty base excipients such as vaseline, vaseline oil, lanolin etc. or self-emulsifiable excipients such as alcohols, fats, polyethylenglycols, ethers or fatty acids esters can be used or other tensides emulsionated in water in the case of unguents, ointments or creams.

On the contrary, in the case of preparation of gels of hydrophilic colloids, polymers of various kind will be used, such as carboxyvinylpolymers, sodium carboxymethylcellulose, methylcellulose, Methocel ® gelled in water, ethanol, propylenglycols, glycerol, poliethylenglycols, etc.

The above mentioned topical preparation can be advantageously added to suitable antibactericides such as parabens, phenol derivatives, quaternary ammonium salts etc.

The active principle concentration will range in these formulations from 1 to 5%.

Some compositions are hereinafter reported, by way of examples.

Formulations in tablets, dosed at 250 mg of active principle:
Compound I: 250 mg
Microcrystalline cellulose (Avicel ®): 20 mg
Lactose: 42 mg
Polyvinylpyrrolidone (PVP): 6 mg
Magnesium stearate: 3 mg
$SiO_2$: 1 mg.

Granules of active principles are prepared with Avicel ®, lactose and an alcoholic solution of PVP; the granulate obtained is dried, then mixed with magnesium stearate and silicon dioxide and the mixture so obtained is pressed in tablets containing each 250 mg of active principle.

Formulations in capsules, dosed at 250 mg of active principle:
Compound I: 250 mg
Maize starch: 100 mg
Lactose: 100 mg
PVP: 6 mg
Magnesium stearate: 5 mg.

The raw materials are sieved, charged in mixer for powders and the mixture is homogenized.

The homogeneous mixture so obtained is destributed in hard gelatine capsules or opercolates by means of a filling machine.

Formulations in suppositories dosed at 375 mg of active principle:
Compound I: 375 mg
Colloidal silica: 8 mg
Semisynthetic glycerides up to (Witepol ®): 2000 mg.

The excipient mass is melt at 40° C.

The active principle is mixed with the molten mass by means of a suitable mechanical dispersing apparatus. The mass is cooled to 36° C. and cast, keeping under stirring the suppository mass, in PVC or aluminium valves.

The mass is allowed to solidify and the containers are suitably sealed.

Formulations in cream dosed at 5% of active principle:

Compound I: 5 g
Octyl dodecanol (Eutanol G ®): 7 g
Liquid $C_8$ tryglyceride (Miritol 318 ®): 3 g
Polyoxyethylen cetostearilic alcohol: 2 g
(Emulgin $B_1/B_2$ ®):
Propylen glycol): 5 g
Carboxyvinylpolymer (Carbopol 940): 1 g
Fenocombin: 1 g
Sodium hydroxide to:
Distilled water to: 100 g.

The carboxyvinylpolymer is dispersed in water (20%) of the amount necessary for the batch preparation) and is neutralized with sodium hydroxide in the amount required to obtain a pH of 5.5.

The fatty phase components are collected in a suitable melter and are melt at the temperature of 70° C.

The active principle is dispersed in glycol and water (10% of the amount necessary for the batch preparation), the preservative agent is dissolved in the residual amount of water and the solution is heated to 80° C.

The aqueous phase is poured in the fatty phase by carrying out the homogenization by means of a suitable emulsifying apparatus. The mixture is cooled at 40° C. and the hydroglycolic suspension of the active principle is added to the emulsion.

Finally the emulsion is stabilized with the CVPolymer gel added and dispersed by means of suitable mechanical stirrer.

The pH is checked and adjusted to 5.5.

The cream is distributed in flexible aluminium tubes or other suitable packaging material for topical use preparations.

I claim:

1. The compound N-cyclohexyl-N''-4-(2-methylthioquinolyl)-N'-2-thiazolyl-guanidine of formula

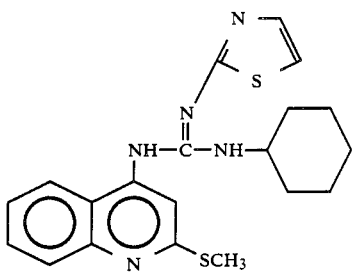

2. A pharmaceutical composition having antiinflammatory, analgesic, antipyretic activity containing as active component a therapeutically effective amount of the compound having formula I

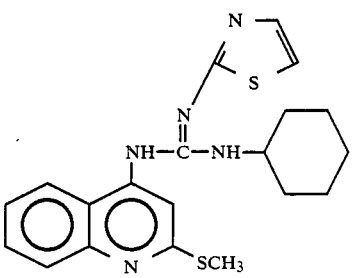

or a non-toxic salt thereof and a pharmaceutically acceptable carrier or diluent.

3. A pharmaceutical composition according to claim 2 for oral, rectal or parenteral administration, in the form of capsules, tablets, suppositories or vials, containing from 100 to 500 mg of said active component per unit dose.

4. A pharmaceutical composition according to claim 2 for topical administration in form of a cream, ointment or gel containing from 1% to 5% of said active component.

* * * * *